United States Patent [19]

Moeller et al.

[11] Patent Number: 4,714,784

[45] Date of Patent: Dec. 22, 1987

[54] METHOD FOR REMOVING N-BUTYRALDEHYDE FROM GAS STREAMS

[75] Inventors: Eckhard Moeller; Wolfgang H. E. Mueller; Manfred Z. Hausen, all of Marl, Fed. Rep. of Germany

[73] Assignee: Hüls Aktiengesellschaft, Marl, Fed. Rep. of Germany

[21] Appl. No.: 886,035

[22] Filed: Jul. 16, 1986

[30] Foreign Application Priority Data

Aug. 6, 1985 [DE] Fed. Rep. of Germany ....... 3528124

[51] Int. Cl.$^4$ .............................................. C07C 45/78
[52] U.S. Cl. .................................... 568/492; 568/449; 568/461; 568/463
[58] Field of Search ................ 568/492, 449, 461, 463

[56] References Cited

U.S. PATENT DOCUMENTS

| | | | |
|---|---|---|---|
| 2,514,966 | 7/1950 | Pierotti et al. | 568/492 |
| 2,684,385 | 7/1954 | Biribauer et al. | 568/461 |
| 4,268,695 | 5/1981 | Lange | 568/864 |
| 4,364,869 | 7/1981 | Muller | 260/410.09 R |
| 4,385,965 | 1/1982 | Muller | 203/075 |
| 4,421,692 | 11/1982 | Hoffman | 260/410.09 R |
| 4,450,300 | 3/1983 | Fischer | 568/462 |
| 4,526,971 | 3/1984 | Distelldorf | 546/186 |
| 4,551,564 | 10/1984 | Otte | 568/834 |
| 4,571,284 | 11/1984 | Muller | 203/014 |

FOREIGN PATENT DOCUMENTS

| | | | |
|---|---|---|---|
| 2045169 | 3/1972 | Fed. Rep. of Germany | 568/492 |
| 0001721 | 4/1973 | Japan | 568/492 |
| 0083433 | 7/1981 | Japan | 568/492 |
| 99257 | 7/1977 | Poland | 568/492 |
| 308999 | 8/1971 | U.S.S.R. | 568/492 |

*Primary Examiner*—Werren B. Lone
*Attorney, Agent, or Firm*—Oblon, Fisher, Spivak, McClelland, & Maier

[57] ABSTRACT

The invention relates to a method for removing n-butyraldehyde from gas streams. It is characterized by washing with dilute aqueous alkali in a mass transfer apparatus. According to the invention, n-butyraldehyde can be removed from gas streams in the proportion of >90%, with operation at 0°–40° C. in the absence of added solubilizing agents.

8 Claims, No Drawings

METHOD FOR REMOVING N-BUTYRALDEHYDE FROM GAS STREAMS

BACKGROUND OF THE INVENTION

1. Field of the Invention

The invention relates to a method of removing n-butyraldehyde from gas streams. It is characterized by washing with dilute aqueous alkali in a mass transfer apparatus.

2. Discussion of the Background

Gas streams containing n-butyraldehyde occur in the production of n-butyraldehyde. When n-butyraldehyde is distilled and condensed, when tanks are filled with n-butyraldehyde, or when n-butyraldehyde or liquids containing it are used for various purposes, outgoing gas will contain n-butyraldehyde.

In order to meet legal and other requirements for protecting workers and the environment, n-butyraldehyde must be thoroughly removed from gas streams, before they are emitted to the environment. In the "Technische Anleitung zur Reinhaltung der Luft" (English translation, "Technical Instructions for Maintaining Air Quality"), n-butyraldehyde is classified in Class 2, and sometimes in Class 1, the latter due to its ready oxidizability to butyric acid. The emission limits for Class 2 substances are 3 kg/hr, and for Class 1 they are 0.1 kg/hr.

According to Ger. AS No. 12 94 950, vapor-phase aldehydes can be separated out from exhaust gases by absorption in high-boiling solvents.

Further, it is known in the art to condense n-butyraldehyde to 2-ethylhexenal by aldol condensation in the gas phase on solid catalysts (Swift, H. E. et al., *J. Catalysts*, 15, 407–416 (1969)). The reaction in this case is carried out at 250° C. with conversions of scarcely above 50%, and with the catalyst rapidly becoming inactivated.

According to U.S. Pat. No. 2,684,385, an extractive distillation with sodium hydroxide can be carried out for aldol condensation of vapor phase n-butyraldehyde. For this, n-butyraldehyde must be heated to its boiling point of 75° C. Although an extraction without auxiliary agents is theoretically possible, this method is successful only with large amounts of solubilizing agents. For a conversion of 78%, a column with 60 separating stages is required.

According to Polish Patent No. 99,257, vapor phase n-butyraldehyde is passed at 100° C. through a mixture of 6% aqueous NaOH and a solubilizing agent comprised of alcohol-rich hydrocarbons, whereby the n-butyraldehyde is condensed to 2-ethylhexenal. For workup of the reaction products, a mixture of 2-ethylhexenal/water azeotrope and alcohols is distilled, and this must be subsequently separated.

The known methods involve aldol condensation of vapor-phase n-butyraldehyde to form 2-ethylhexenal. They require high temperatures, and the use of aqueous alkalis. They also require additional solubilizing agents. These agents to some extent complicate the isolation of the 2-ethylhexenal as an economic product. No method is known whereby over 90% of the n-butyraldehyde can be removed from gas streams, with the formation of 2-ethylhexenal, in the absence of solubilizing agents.

SUMMARY OF THE INVENTION

Accordingly, one object of the present invention is to remove n-butyraldehyde from gas streams to a very substantial extent, in an economically feasible process.

Another object of the present invention is to recover n-butyraldehyde or a derivative thereof as an economic product, at minimal cost.

These objects and other objects which will become apparent from the following description of the invention are achieved according to the method of the present invention in which n-butyraldehyde-containing gas streams are washed with a dilute aqueous alkali solution, without solubilizing agents, at 0°–40° C. in a simple mass transfer apparatus.

DETAILED DESCRIPTION OF THE PREFERRED EMBODIMENTS

The gas streams from which the n-butyraldehyde is to be removed may be comprised of air, nitrogen, carbon monoxide, hydrogen, methane, and other gases and gas mixtures which are inert under the given conditions.

The preferred washing temperature is 10°–30° C.

Ordinary liquid/gas mass transfer equipment may be used for the method, for example, stirred tanks, bubble columns, or countercurrent equipment. Countercurrent units such as plate columns or packed columns, having 1 to 15 separating stages, are well suited. Columns with 5–10 actual plates are preferred. Especially preferred are bubble tray towers with 5–10 actual plates.

Suitable aqueous alkalis are 0.5–10 wt. % alkali solutions with the alkali being, for example, NaOH or KOH. Preferably, 2–10% NaOH or KOH is used.

The inventive method achieves very substantial removal of n-butyraldehyde from a gas stream. The amount of n-butyraldehyde removed from the gas stream is generally >90%, and may be >98%. The equipment costs are low, because the equipment is simple and the method is carried out at low temperatures, with dilute alkalis, and with no solubilizing agents.

An organic phase separates out above the alkali flowing out of the mass transfer apparatus. This organic phase can be readily removed. Greater than 90% of it comprises 2-ethylhexenal, which can be further purified in simple fashion. After the organic phase is removed, the alkali can be returned to the apparatus.

The 2-ethylhexenal obtained in this process can be hydrated to produce 2-ethylhexanol, which is of interest as a plasticizer.

Other features of the invention will become apparent in the course of the following descriptions of exemplary embodiments which are given for illustration of the invention and are not intended to be limiting thereof.

EXAMPLE

General experimental conditions

A nitrogen stream containing n-butyraldehyde is passed through a bubble plate column with a diameter of 80 mm having a surface of glass, under normal pressure. The gas stream is passed countercurrent to a dilute NaOH solution, and has the same temperature as the column. The NaOH solution bottoms are recycled after separation from the organic phase which forms.

The experimental conditions and measured parameters are summarized in Table 1. The inventive Examples are designated by numbers, and the comparison examples by letters.

Obviously, numerous modifications and variations of the present invention are possible in light of the above teachings. It is therefore to be understood that within the scope of the appended claims, the invention may be practiced otherwise than as specifically described herein.

TABLE 1

| Example number | No. of actual plates | Temperature °C. | Concentration of the NaOH, wt. % | Gas throughput, m³ of nitrogen per hr (at S.T.P.) | Throughput of alkali solution, liters/hr | Initial concentration of n-BA in the gas, g/m³ (S.T.P.) | Final concentration of n-BA in the gas, g/m³ (S.T.P.) | Degree of removal of the n-BA % |
|---|---|---|---|---|---|---|---|---|
| 1 | 1 | 23 | 10 | 203.2 | 15 | 384.2 | 23.3 | 94.62 |
| 2 | 1 | 23 | 10 | 203.2 | 15 | 809.4 | 46.0 | 95.68 |
| 3 | 1 | 24 | 10 | 201.2 | 15 | 1751.1 | 120.8 | 96.73 |
| 4 | 5 | 23 | 10 | 255.8 | 15 | 447.7 | 8.49 | 98.36 |
| 5 | 5 | 23 | 10 | 216.6 | 15 | 912.8 | 6.03 | 99.53 |
| 6 | 5 | 26 | 10 | 205.4 | 15 | 1634.0 | 21.57 | 99.35 |
| 7 | 10 | 24 | 10 | 199.6 | 15 | 465.9 | 2.0 | 99.63 |
| 8 | 10 | 24 | 10 | 206.7 | 15 | 907.9 | 1.3 | 99.90 |
| 9 | 10 | 26 | 10 | 203.2 | 15 | 1733.7 | 1.5 | 99.96 |
| A | 1 | 50 | 10 | 200.8 | 15 | 435.4 | 156.3 | 67.37 |
| 10 | 5 | 34 | 10 | 323.8 | 15 | 1819.0 | 64.82 | 98.42 |
| B | 10 | 45 | 10 | 140.3 | 15 | 482.4 | 82.6 | 85.06 |
| 11 | 5 | 22 | 2 | 214.0 | 15 | 445.3 | 5.88 | 98.86 |
| 12 | 5 | 27 | 2 | 202.8 | 15 | 908.0 | 11.53 | 99.09 |
| 13 | 5 | 28 | 2 | 193.6 | 15 | 1625.0 | 19.81 | 99.39 | n-BA = n-Butyraldehyde
S.T.P. = Standard temperature and pressure

What is claimed as new and desired to be secured by Letters Patent of the United States is:

1. A method for removing n-butyraldehyde from gas streams, comprising washing a gas stream at 0°–40° C. with a 0.5–10% by weight aqueous alkali solution in the absence of solubilizing agents.

2. The method of claim 1, wherein said washing step is carried out at 10°–30° C.

3. The method of claim 1, wherein said aqueous alkali solution is 2–10% by weight.

4. The method of claim 3, wherein said aqueous alkali solution is a 2–10% solution of NaOH, KOH or mixtures thereof.

5. The method of claim 1, wherein said aqueous alkali solution is recycled.

6. The method of claim 1, wherein said washing step is carried out countercurrently.

7. The method of claim 6, wherein said washing step is carried out in a column with 5–10 actual plates.

8. The method of claim 7, wherein said column is a bubble plate.

* * * * *